US008838217B2

(12) United States Patent
Myr

(10) Patent No.: US 8,838,217 B2
(45) Date of Patent: Sep. 16, 2014

(54) SYSTEM AND APPARATUS FOR PROVIDING DIAGNOSIS AND PERSONALIZED ABNORMALITIES ALERTS AND FOR PROVIDING ADAPTIVE RESPONSES IN CLINICAL TRIALS

(75) Inventor: David A. Myr, Jerusalem (IL)

(73) Assignee: Makor Issues and Rights Ltd., Jerusalem (IL)

( * ) Notice: Subject to any disclaimer, the term of this patent is extended or adjusted under 35 U.S.C. 154(b) by 866 days.

(21) Appl. No.: 12/615,445

(22) Filed: Nov. 10, 2009

(65) Prior Publication Data

US 2011/0112416 A1    May 12, 2011

(51) Int. Cl.
*A61B 5/00* (2006.01)
*A61B 5/04* (2006.01)

(52) U.S. Cl.
CPC ............................. *A61B 5/0006* (2013.01)
USPC ........................ 600/509; 600/513; 600/515

(58) Field of Classification Search
USPC ........................................ 600/509, 513, 515
See application file for complete search history.

(56) References Cited

U.S. PATENT DOCUMENTS

| | | | | |
|---|---|---|---|---|
| 4,883,065 A | * | 11/1989 | Kelen | 600/524 |
| 5,036,856 A | | 8/1991 | Thornton | |
| 5,312,446 A | * | 5/1994 | Holschbach et al. | 607/9 |
| 5,357,427 A | * | 10/1994 | Langen et al. | 600/300 |
| 5,398,183 A | | 3/1995 | Elliott | |
| 5,433,209 A | | 7/1995 | Gallant et al. | |
| 5,447,161 A | | 9/1995 | Blazek et al. | |
| 6,004,276 A | * | 12/1999 | Wright et al. | 600/508 |
| 6,117,077 A | * | 9/2000 | Del Mar et al. | 600/301 |
| 6,463,320 B1 | * | 10/2002 | Xue et al. | 600/523 |
| 6,605,046 B1 | * | 8/2003 | Del Mar | 600/507 |
| 6,632,181 B2 | | 10/2003 | Flaherty et al. | |
| 6,701,184 B2 | | 3/2004 | Henkin | |
| 6,773,396 B2 | | 8/2004 | Flach et al. | |
| 6,869,404 B2 | * | 3/2005 | Schulhauser et al. | 600/528 |
| 7,074,183 B2 | * | 7/2006 | Castellanos | 600/300 |
| 7,301,452 B2 | | 11/2007 | Gerder et al. | |
| 7,353,179 B2 | | 4/2008 | Ott et al. | |
| 7,429,245 B2 | | 9/2008 | Whitaker et al. | |
| 7,787,946 B2 | * | 8/2010 | Stahmann et al. | 607/3 |
| 7,878,198 B2 | * | 2/2011 | Farrell et al. | 128/204.18 |
| 7,978,062 B2 | * | 7/2011 | LaLonde et al. | 340/539.11 |

(Continued)

OTHER PUBLICATIONS

M. Fisher, *Holter Monitoring in Patients with Transient Focal Cerebral Ischemia*, 4 pages, 1978 American Heart Association, Dallas, Texas.

(Continued)

*Primary Examiner* — Niketa Patel
*Assistant Examiner* — Christopher A Flory
(74) *Attorney, Agent, or Firm* — RatnerPrestia

(57) ABSTRACT

A personalized real-time automated cardiovascular monitoring system monitors abnormalities in a patient's cardiovascular activity data through the use of individually adjusted electrocardiogram Holter apparatus (Holter/ECG device) that provides an automatic medical diagnosis of cardiac abnormalities and generates abnormality alert signals representative of certain abnormalities in patient's cardiac activities. The signals are transmitted using a wireless network to a medical dispatcher center. A response is generated according to the abnormality detected. Individual parameters indicative of patient's cardio activities are personalized to allow for adjustments of chronic patients. A base Holter/ECG unit, includes the wireless/electric electrodes and their respective wireless/electric connections, and a Holter/ECG recording unit affixed to the base unit. Automatic real-time medical response may be provided based on automatic cardiac abnormality alert detection from the Holter/ECG data.

20 Claims, 7 Drawing Sheets

(56) References Cited

U.S. PATENT DOCUMENTS

| | | | |
|---|---|---|---|
| 2002/0016719 A1* | 2/2002 | Nemeth et al. | 705/2 |
| 2004/0093240 A1 | 5/2004 | Shah | |
| 2005/0038692 A1 | 2/2005 | Kane et al. | |
| 2005/0055241 A1 | 3/2005 | Horstmann | |
| 2005/0115561 A1* | 6/2005 | Stahmann et al. | 128/200.24 |
| 2005/0203777 A1* | 9/2005 | Rosenfeld et al. | 705/3 |
| 2006/0100530 A1 | 5/2006 | Kliot et al. | |
| 2006/0161459 A9* | 7/2006 | Rosenfeld et al. | 705/3 |
| 2006/0250260 A1* | 11/2006 | Albert et al. | 340/628 |
| 2007/0008153 A1* | 1/2007 | Albert | 340/573.1 |
| 2007/0032733 A1* | 2/2007 | Burton | 600/509 |
| 2007/0096927 A1* | 5/2007 | Albert | 340/573.1 |
| 2007/0156459 A1 | 7/2007 | McMahon et al. | |
| 2007/0167850 A1* | 7/2007 | Russell et al. | 600/513 |
| 2007/0265881 A1 | 11/2007 | El Eman et al. | |
| 2008/0021341 A1 | 1/2008 | Harris et al. | |
| 2008/0051667 A1* | 2/2008 | Goldreich | 600/481 |
| 2008/0161707 A1* | 7/2008 | Farringdon et al. | 600/509 |
| 2008/0183082 A1* | 7/2008 | Farringdon et al. | 600/481 |
| 2008/0224852 A1 | 9/2008 | Dicks et al. | |
| 2008/0228057 A1 | 9/2008 | Graskov et al. | |
| 2008/0270181 A1 | 10/2008 | Rosenberg | |
| 2009/0058635 A1* | 3/2009 | LaLonde et al. | 340/539.11 |
| 2009/0058636 A1* | 3/2009 | Gaskill et al. | 340/539.11 |
| 2009/0062887 A1* | 3/2009 | Mass et al. | 607/60 |
| 2009/0063193 A1* | 3/2009 | Barton et al. | 705/3 |
| 2009/0069642 A1* | 3/2009 | Gao et al. | 600/300 |
| 2009/0112769 A1 | 4/2009 | Dicks et al. | |
| 2009/0115628 A1 | 5/2009 | Dicks et al. | |
| 2009/0318779 A1* | 12/2009 | Tran | 600/301 |
| 2010/0198124 A1* | 8/2010 | Bhugra | 602/5 |
| 2010/0198613 A1* | 8/2010 | Weller et al. | 705/2 |
| 2011/0190595 A1* | 8/2011 | Bennett et al. | 600/301 |

OTHER PUBLICATIONS

*Mobile Telemedicine* (12 leads ECGs transmitted to the Medical Center from Ambulance), 3 pages, http://www.kuronowish.com/~davinci333/mobiletelemedicine/.

*M12R Ambulatory 12 lead Electrocardiograph* (Holter Recording and Bluetooth Wireless ECG data transmission functions), 2 pages, http://www.globalinstrumentation.com/GIMedical/Brochures/001-700-0106__A%20(M12R%20Holter%20Recorder%20Sales%20Brochure).pdf.

* cited by examiner

FIG. 3

| disease | indicator | unit | smaller than | greather than | equal |
|---------|-----------|------|--------------|---------------|-------|
| 1 | X | per min | | | |
| 2 | Y | per sec | | | |
| - | - | - | | | |
| N | Z | % | | | |

SYSTEM AND APPARATUS FOR PROVIDING DIAGNOSIS AND PERSONALIZED ABNORMALITIES ALERTS AND FOR PROVIDING ADAPTIVE RESPONSES IN CLINICAL TRIALS

FIELD OF THE INVENTION

The present invention relates to cardiac monitoring system and, more particularly, to a Holter/ECG-type system and apparatus for real-time automated diagnostics of the cardiological activity of the patient. The present invention also relates to a system for providing real-time medical response in clinical trials.

BACKGROUND OF THE INVENTION

In general, there are two types of cardiovascular abnormalities tests: a one-time recording during a few seconds and a long-term monitoring which can be performed during regular daily activities or as a round-the-clock monitoring in patients with serious medical disturbances. An example of a one-time recording is an electrocardiogram (ECG) test. However ECG test is not sufficient comprehensive because it tests only a brief period of time, and therefore can detect only a part of cardiovascular abnormalities.

A prime example of long-term monitoring system is a 24-hour cardiovascular monitoring Holter system which is widely used in the prior art for diagnosing cardiac abnormalities. Currently used Holter recording devices use an analogue or digital recording technique. Data recorded by such a holter was initially analyzed by a medical professional, which amounts to many hours of expensive manual labor. One such basic Holter ECG system disclosed by Elliott in U.S. Pat. No. 5,398,183, another one by Thornton in U.S. Pat. No. 5,036,856.

As a next development of holter technology, computerized data analysis was introduced. Usually, in current digital Holter systems, processing of the data consists of computerized data scanning to receive the preliminary diagnosis with subsequent manual verification by a medical professional.

Such Holter system had been developed by several companies worldwide:
Burdick Vision holters by CardiacScience Inc, a US company;
FM Series holters by a Japanese company Fukuda;
DL Series holters by Braemar Inc, another US company;
H-Scribe holter by Mortara, another US company;
DR 180 holter by NEMon;
Reveala by Nasan Medical, an Indian company; to name a few.

Holters mentioned above provide mainly data recording.

Lately, there have been further developments in the holters industry. A number of modern holters are now equipped with data analysis software. An example of such a holter is a Trillium 3000 by Forest Medical. In this holter all cardiological data is recorded over the 24 hours period, and at the end of the 24 hours period a report is generated using data analysis tool. This report is further printed and the printed report is presented to the physician for his review. Another example of a holter with analyzing capabilities is the one presented by the Epicardia Holter Systems, where after finishing data recording, the technician can scan the recorder data and generate a report on events detected.

An example of Holter system with analysis capabilities was presented by Gallant in U.S. Pat. No. 5,433,209 named "Recorder unit for ambulatory ECG monitoring system".

As a further development of holter systems, there are products that provide transfer of cardiological data recorded through the Internet or through the wireless device to the clinic. I.e., data is recorded for, say, 24 hours and then, instead of visiting the clinic, the patient has to connect to the Internet at his home computer and send the data to the medical center through the Internet. Alternatively, in other products the patient has to send the data from his holter to the medical center through wireless device. In both cases above, the medical diagnosis and, consequently, alert on cardiovascular abnormality is in the clinic and not in real-time. An example of such a holter is a Vision Premier developed by Burdick company, which includes connectivity between the holter and various information systems, including the suite of HeartCentrix web data management solutions. An example of holter data transmittance through the wireless system is presented by HealthPAL device from MedApps company that automatically collects data from compatible, off-the-shelf, medical monitors using a smart cable or wirelessly via Bluetooth. The data is then transmitted using embedded M2M (GSM and CDMA) cellular chip technology to be received by HealthCOM, MedApps' full-featured, web-based portal for health care providers.

U.S. Pat. No. 6,701,184 titled "Virtual Holter" by Henkin describes such holter that provides "ECG Holter data scanning, processing, and analyzing system by way of obtaining a Holter recording in a conventional manner, then downloading that analog or digital data to a PC, then going online through the PC by way of an ISP, such as DSL, capable of large data transfer, through a USB to tie into a URL web address for a Central Computing Facility . . . ". One further similar system disclosed in U.S. Pat. No. 7,353,179 titled "System and method for handling the acquisition and analysis of medical data over a network" by Ott. Ott describes a system that receives and controls Holter data from remote computers associated with the patients.

An example of Holter ECG system that uses a cellular architecture to monitor and to transfer ECG signals via cellular network presented by Flach in U.S. Pat. No. 6,773,396 named "Cellular architecture and data transfer methods for real time patient monitoring within medical facilities". One more example of a similar system presented by Gerder in U.S. Pat. No. 7,301,452 titled "Care device with wireless data communication". US 20090115628, 20090112769 and 20080224852 by Dicks describe a system configured to wirelessly receive data from a medical device using the medical device transceiver and transmit the data to an intermediary device using the data relay transceiver.

US patent application 20060100530 by Kliot titled "Systems and methods for non-invasive detection and monitoring of cardiac and blood parameters" discloses a "Method and system for long term monitoring of one or more physiological parameters such as respiration, heart rate, body temperature, electrical heart activity, blood oxygenation, blood flow velocity, blood pressure, intracranial pressure, the presence of emboli in the blood stream and electrical brain activity are provided." Kliot in his system actually provides a possibility of alert and "localization capabilities incorporating VHF, GPS, satellite and/or triangulation location systems," but his system is limited to physiological parameters such as respiration, heart rate, body temperature, etc. and is not a holter system. Actually, Kliot mentions holters in his prior art paragraphs as: "Although Holter and cardiac event monitors are being used in attempts to diagnose and monitor various cardiac irregularities that are asymptomatic or infrequently experienced, their limited data storage and analysis capabilities have reduced their application for wider ranging diagnostic and monitoring applications. The success rate is rather low with these devices, since the Holter monitor seldom captures rare events in the typical, relatively short-term recording period and event monitor is patient-triggered and user dependent. These systems could be improved with more substantial recording and data storage capability and better analytical systems. The Holter and cardiac event monitors also are typically operated as stand-alone devices and are not interfaced with other devices collecting clinically useful patient data. Nonetheless, Holter and cardiac event monitoring are the only longer-term cardiac event monitoring systems presently available."

As a most sophisticated development of holters, there are a few that provide cardiovascular data analysis of several major cardiological diseases and sent the data analyzed through wireless network. The most advanced of such a product is a Cardionet which presents the "Mobile Cardiac Outpatient Telemetry" product with real time analysis, automatic arrhythmia detection and wireless ECG transmission.

Clinical trial management is a second major aspect of the invention.

Effective clinical trial management systems relies on a means of real-time collection of data and performance measures to be able to react instantly to the changes in performance of medicine or treatment in the clinical trial participant, which is very important when relevant information belongs to the clinical trial where participant location may be very diverse geographically. This is especially true in clinical trials of new medicines as clinical evaluations of new pharmaceuticals in particular involve numerous evaluations at different stages of development that often involve many sites spread throughout different countries and time zones.

Currently, clinical trial data mainly manually recorded on paper or entered manually via a keyboard to the computer. Alternatively, "paperless" data may be entered directly into a computer at a remote site, in either manual or automated way. With advancements in computer science there had been some advancement in clinical trials field. There are a number of prior art citations that disclose real-time clinical trial systems. One such example is provided by El Eman in US patent application 20070265881. El Eman discloses a system where real-time interactive patient form is introduced. Clinical trial participants insert data related to the clinical trial via the XML web-based form and they can transfer it via the web to the centralized database of a clinical trial. Another similar system is disclosed in US patent application 20050055241 by Horstmann wherein a real-time clinical trial study documentation is provided and where a change to the documentation by an authorized user is made available in real time to one or more other authorized users for tasks relating to the clinical trial study documentation. Another example of a similar system was disclosed in a US patent application 20050038692 by Kane titled "System and method for facilitating centralized candidate selection and monitoring subject participation in clinical trial studies" wherein centralized remote ratings of subjects in clinical trial studies are introduced to determine whether a candidate is a qualified subject for the clinical trial and/or in the actual assessment, or information collection, phase of the clinical trial. US patent application 20040093240 by Shah provides real-time clinical trial status monitoring at definable intervals and it is another variant of the prior art type above.

As a further development in the clinical trials industry, currently there are a few prior art citations where wireless data communication has been introduced. For one, US 20080228057 titled "Method and system for controlling data information between two portable apparatuses" by Graskov discloses a method and system of controlling data information between two portable handheld apparatuses where information gathered throughout the clinical trial could be transferred wirelessly, and in particular "lipid monitor, a pulse monitor, a lancet device, a storage container, and a blood glucose monitor (BGM)." Unlike our disclosed invention, no cardiological data is introduced here and no real-time and adaptive clinical trial features could be seen here. Another such system is presented in US 20070156459 by McMahon that discloses a system for conducting a clinical trial of a pharmaceutical substance on a plurality of trial participants that includes a central database and the remote computers being configured to receive predetermined trial data from one or more trial participants. Yet another similar system is presented in US 20080021341 titled Methods and Systems for Facilitating Clinical Trials by Harris that involves a clinical trial for experimental therapies rather than for the pharmaceutical substance.

More sophisticated approach is presented in several prior art patent applications wherein the data is collected wirelessly. One such prior art invention is US patent application 20080270181 titled "Method and system for collection, validation, and reporting of data and meta-data in conducting adaptive clinical trials" by Rosenberg. In 20080270181 Rosenberg describes a system for centrally managing data in an adaptive clinical trial or other adaptive process that is conducted at a plurality of geographically remote sites. Rosenberg discloses a system that collects data from remote sites in a clinical trial by the means of internet, telephone, wireless system, RSS feed or Atom feed. The system also provides interaction between central and remote sites to manage and resolve data discrepancies. The invention provides some improvement on the abovementioned since it provides some ability to collect and process various forms of data in order to adjust actions related to the clinical trial but it still maintains the shortcomings of the prior art above. The data is not collected in real-time but rather collected through the patient's visit to the remote clinical site and then the data could be transmitted by internet, wirelessly, etc. Still, unlike our invention, no real-time and personalized cardiological data analysis, response and adaptation are made.

An additional element of our invention is an alert-triggered permanent blood pressure measurement system.

Currently blood pressure measurement is done mainly when the patient is visiting the physician or using a regular self-measurement home blood pressure measurement device. Those measurements methods required an improvement since blood pressure results could vary during several one-time measurements. Some 25% of the patients have higher blood pressure when visiting the physician, for example. Accordingly, ambulatory blood pressure monitors systems have been created, one of those by a German manufacturer Ergoline named Ergoscan 24, another is by Chinese manufacturer Contectmed "CMS06C ABPM Ambulatory Blood Pressure Monitoring System".

Additionally, there are a number of prior art inventions on the matter of ambulatory blood pressure systems and devices known in the prior art. For one, there is a U.S. Pat. No. 7,429,245 by Whitaker titled "Motion management in a fast blood pressure measurement device". That invention discloses an apparatus and a method for measuring the blood pressure of a vertebrate subject that uses an inflatable chamber with a sensor to detect signals indicative of a blood pressure of the subject during an inflation interval of the inflatable chamber. If secondary motion or artifact signals are detected, the apparatus and method determine whether the secondary signals are below a predetermined value, and if so, complete the measurement.

Another U.S. Pat. No. 5,447,161 discloses: "a process and measurement device for noninvasive determination of venous and arterial blood pressure in the arteries of the human body, particularly in the finger and toes. An occlusion band and peripherally thereto a sensor for the detection of changes in the blood volume during the pressure-buildup procedure is attached in these measurement areas".

Another U.S. Pat. No. 6,632,181 titled "Rapid non-invasive blood pressure measuring device" by Flaherty discloses a blood pressure ambulatory measurement device that works by supplying an external pressure to a portion of an artery and where the external pressure is preferably between the systolic and diastolic pressure.

BRIEF DESCRIPTION OF THE DRAWINGS

FIG. 3 graphically illustrates the personalized alerts thresholds for every patient enrolled.

DETAILED DESCRIPTION OF THE INVENTION

Figure 1:
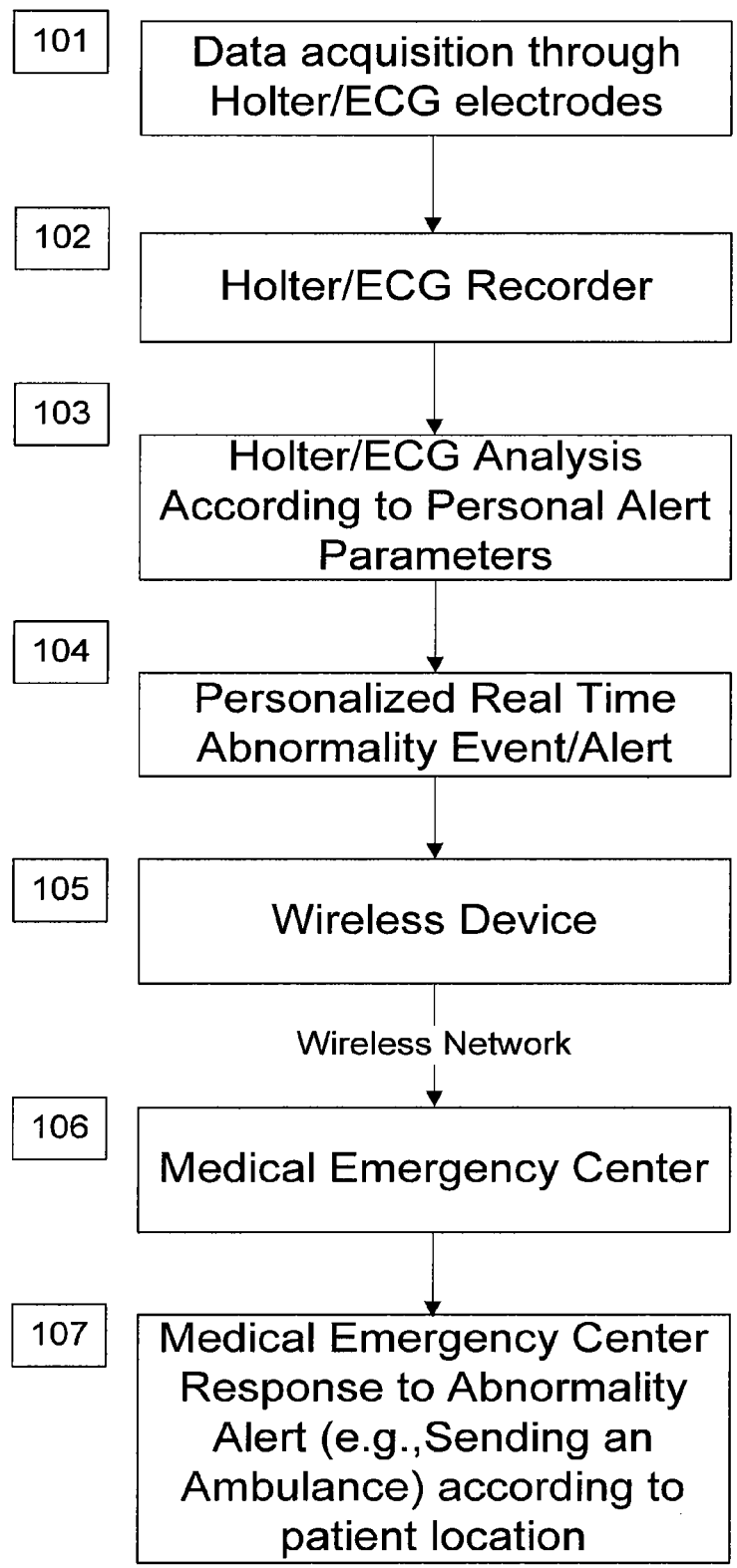
FIG. 1 provides a general overview of the invented system and apparatus.

In the following discussion, numerous specific details are set forth to provide a thorough understanding of the present invention.

The invention deals with two major aspects: as a first aspect, it provides a real-time automated cardiovascular personalized monitoring system for permanently monitoring the abnormalities in patient's cardiovascular data through the use of permanent Holter/ECG device and generating alert signals representative of certain abnormalities of the patient according to individual alert parameters adjusted for every patient enrolled; as a second aspect it provides a system for quick real-time (or very near real-time) response in clinical trials to the adverse effects related to use of medications, as well as to the abnormalities alerts in general, as detected by the personalized cardiovascular monitoring system of the first aspect.

The above-mentioned prior art examples lack the feature of event-triggered blood pressure measurements which could be particularly important to chronic heart patients as well as other patients with heart disease developments. This feature will help physicians and clinical trial investigators know the blood pressure measurements at the exact time when an abnormality cardiac alert is detected by the Holter/ECG software.

Other features and advantages of the present invention will be apparent from the following description taken in conjunction with the accompanying drawings, in which like reference characters designate the same or similar parts throughout the figures thereof.

A Holter Electrocardiogram—often referred to as Holter EKG or ECG—is a test that measures the electrical activity of the heart for a prolonged period of time, typically 24 or 48 hours, on an outpatient basis. Holter differs from a resting ECG in that a resting ECG records a very small portion of your heart's activity, less than one quarter of one percent of your daily heartbeats. The resting ECG is taken while you are at rest and, therefore, does not show how your heart will react to normal daily life.

Every patient enrolled into the disclosed system receives the Holter/ECG device for the permanent use and it works continuously even when the patient does not feel any pain or other uncomfortable symptoms.

The system includes a number of Holter/ECG electrodes/sensors, which are affixed to the patient and they generate signals indicative of certain cardiovascular activities being carried out by the patient (101). These signals could be obtained by the means of either digital or analogue Holter/ECG. In case where they are obtained by the means of analogue Holter/ECG, they will be then digitized. In such a case an analogue-digital converter will be used to convert the analogue signal to the digital signal.

Cardiac activity of the patient obtained from the electrodes will be recorder by the Holter/ECG recorder (102).

The patient's cardiovascular activities recorded by 102 will then be analyzed by Holter/ECG personalized analysis software (103). This special personalized Holter/ECG software will be used in decoding of the cardiovascular data of the patient and, following that will detect abnormalities in the Holter/ECG signals automatically, in real-time and in accordance to the personal cardiological and general medical data of the patient (104). Such personalized adjustments are especially important for the chronic patients.

Those abnormalities will be classified according to their severity classification—some abnormalities will only be stored in a file of the particular patient, others will require him to take a medicine, others will require a visit to the doctor, while others will require calling an ambulance without any delay. A special medical classification of Holter/ECG-detected abnormalities will be applied. Such medical classification will be produced by the medical experts and in accordance with the usual cardiovascular medical classifications, such as the Minnesota Code.

Such Holter/ECG software will be integrated inside the wireless device (as a part of it) capable of bi-directional transmittance of information in a wireless phone network. The software will be built-in as a chip on the board of such a wireless device. A regular existing cellphone handset provides an example of such wireless device (105).

Such wireless device will send abnormalities alerts detected wirelessly, using cellular network, to a medical dispatcher center (106).

A real-time medical response such as sending an ambulance will be generated by the medical emergency center according to those automatically detected signals in accordance with abnormalities classification (107). Actually, each abnormality alert will be classified according to the severity of the disease alerted. When the abnormality detected justifies an urgent alert, the Holter/ECG will use the cellular network to transfer the emergency signal to the medical center. There the signals will be attended by the medical dispatcher. This will allow the dispatcher working in the center to send ambulance to the patient according to his location detected by the means of GPS or/and cellular network location.

Figure 2:
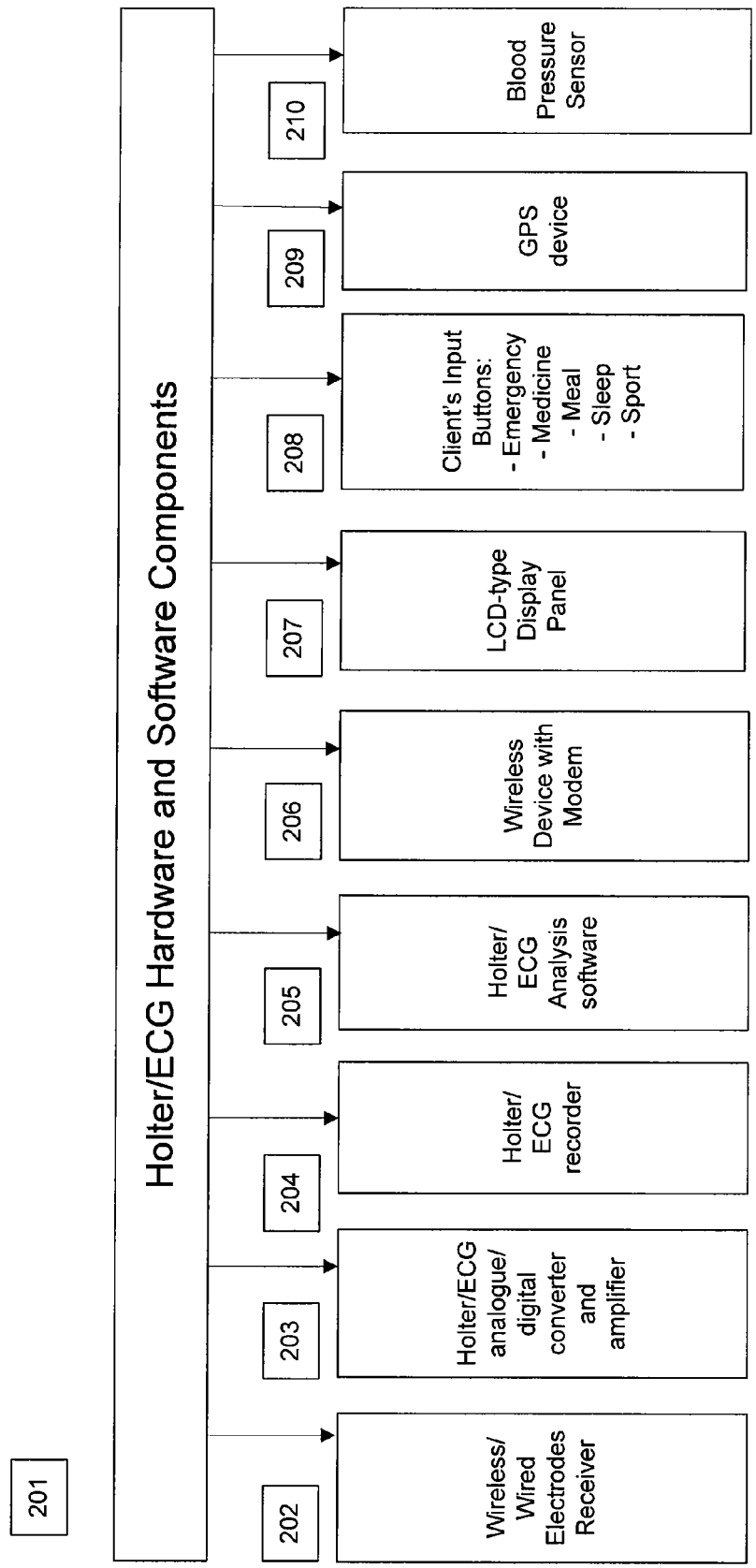
FIG. 2 shows the major hardware and software components of the invented system and apparatus.
Figure 4:
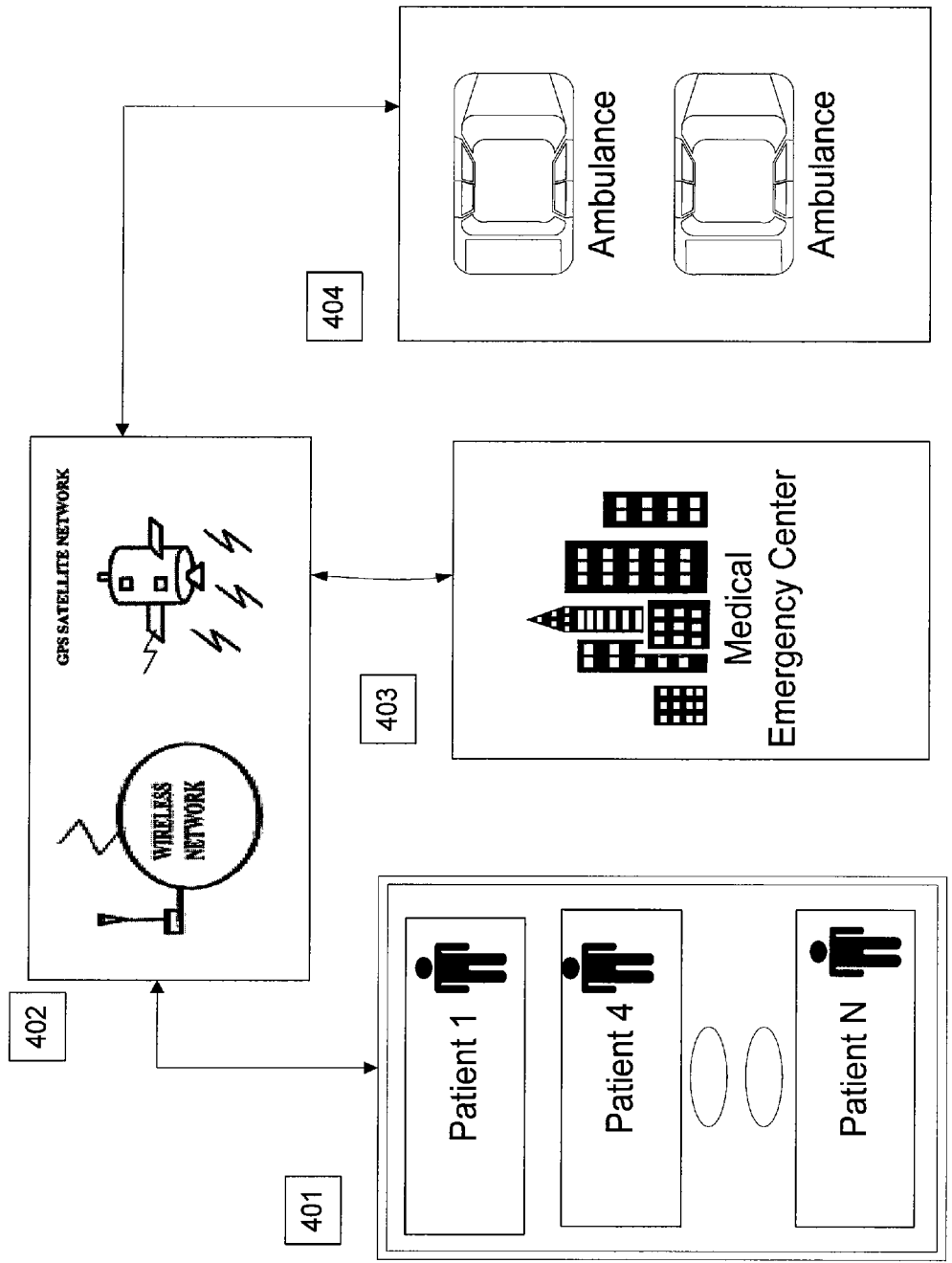
FIG. 4 is a schematic representation of the bi-directional communication data exchange between Holter/ECG of the patients and medical emergency services.

FIG. 2 graphically summarizes major hardware and software components in the invented system and apparatus (201).

202 illustrates recording of physiological signals corresponding to cardiac activity collected by external electrodes applied to a patient, comprising a set of electrodes. Preferably, a 12-lead electrode system will be used for more accurate cardiac signals collection.

203 show a Holter/ECG converter and amplifier hardware components. An analogue-digital converter will be used only in case of analogue Holter/ECG to convert the analogue signal to the digital signal.

204 show a Holter/ECG recorder. A regular Holter/ECG recorder could be used in the invented system. It will be well understood by those skilled in the art that each regular Holter/ECG recorder will provide merely an exemplary component, and that the present invention is by no means limited to any particular Holter/ECG recorder. The holter is equipped with the first-in first-out feature, wherein the data recorded first will be deleted first and the data recorded last will be deleted last.

205 show a Holter/ECG personalized analysis software used to analyze the patient's cardiovascular activities to detect abnormalities. The software is capable of analyzing and detecting widely known cardiac abnormalities. The software is also capable of multiple ECG scanning modes for reviewing data and capturing cardiac abnormalities. On any stage the software is able to produce as an output a final report with summary of all cardio action recorded and with details regarding all cardiological abnormalities detected. The software provided to each patient will be personalized according to personal health, age and sex characteristics. For such personalization, each patient enrolled into the system will have to complete the personal questionnaire where he will indicate his usual blood pressure, pulse, and other vital signs. To this initial enrollment questionnaire, the doctor will add recent ECG data of this patient.

Based on this initial enrollment data, for each patient and for each cardiological disease there will be defined a predetermined set of threshold parameters, different every indicator indicative of a certain disease, each of said threshold alert parameters being individually adjustable by the physician during the operation of the holter. This is of importance since there are many chronic patients that for them the basic default threshold alert parameters will produce many alerts that are not of any clinical significance. Therefore, ECG recording of such chronic patient will differ significantly from the ECG recording of a completely healthy person. For a simple example, for the person with usual heart beats rate of 100 per minute, sinus tachycardia alert threshold should be placed not at 100 but, lets say at 120 heart beats per minute.

Additionally to the personally adjusted alert threshold parameters, alert parameters will be adjusted when the person has taken a medicine, a meal, has been engaged in sporting activity or has been asleep. This information will be recorded when the patient will push the Medicine, Meal, Sports and Sleep buttons—Medicine that will be pressed when the patient has taken any particular medicine, Sports that will be pressed when the patient will be engaged in a sporting activity; Meal that will be pressed when the patient will have a meal; Sleep that will be pressed when the patient will start/finish his sleep; additionally an Emergency button will be provided for quick contact of the emergency center. Initial personalized abnormality "resting" alert thresholds will be then updated based on the inputted patient data above.

Personalized abnormalities alerts thresholds will also be updated in real-time during the ongoing permanent Holter/ECG monitoring by taking into consideration a new cardiological data obtained on the patient, analyzing such data, including a relevant personal abnormalities alerts thresholds, and producing a new personal alerts thresholds based on this data. This will be done by initially obtaining as an input from the centralized database initial patient personalized emergency alerts thresholds, then obtaining as an input a real-time cardiological data of the patient from the Holter/ECG monitoring, including patient personalized emergency alerts thresholds previously taken and, then, by updating said patient personalized emergency alerts thresholds with the newly obtained data during the real-time Holter/ECG cardiac monitoring (FIG. 3 graphically illustrates the personalized alerts thresholds for every patient enrolled).

By looking at the abovementioned example, sinus tachycardia alert threshold will be different for the same person at resting status and person at "Sports" status as heart beats rate is different for the same person at resting status and at "sports" status.

The collected ECGs contain certain types of noise, which are typical for Holter ECG recordings. Such noise is the baseline noise (e.g. respiration), high frequency noise, line frequency noise, beat-like artifacts (because of temporary pressure on electrodes) and high range noise (in case electrodes become loose). The modern holter/ECG analysis software can analyze, recognize and cutout the noise elements to provide more accurate analysis and detection. Noise removal is an important part of getting a correct cardiovascular diagnosis.

Element 206 shows the wireless device equipped with the modem and cellphone antenna capable of transmitting data.

Element 207 shows the LCD-type or touch screen display panel that the wireless device 206 equipped with.

Element 208 shows the custom-made client's input buttons of this configuration of the wireless device 206 as the system is provided with input capability for enabling the patient to input data such as the time of meal intake, time of sleep, etc.

Element 209 illustrates that the wireless device 206 can be configured with the GPS location data transmitter/receiver as well as a user communication device. It should be noted that in this configuration GPS capabilities are an advantage but not absolutely necessary for navigational directions.

Element 210 illustrates that a special blood pressure system will be incorporated inside the invented system and device. High blood pressure is a common risk factor for heart attacks, strokes and aneurysms, so permanent monitoring is critically important. Additionally, in clinical trials it is important to use this feature, especially when it is necessary to see how well your medicine is working to control your high blood pressure. The blood pressure system will consist of blood pressure sensor, blood pressure recorder and inflatable cuff chamber. The system will work on a permanent basis and it will measure the blood pressure at event-triggered basis, i.e. it will measure blood pressure when the holter/ECG will detect an abnormality event (blood pressure measurements at predetermined time intervals, say once an hour will also be made). This will help to diagnose a correct cardiological disease and to indicate long-time blood pressure measurements. For the purpose of permanent blood pressure monitoring, a non-invasive blood sensor will be used. A solid, small-sized blood pressure sensor, preferably cuff-less, worn over a palpable artery could be utilized to measure arterial blood pressure.

As abovementioned, the system will further include the wireless architecture and infrastructure as an integral part of the disclosed Holter/ECG system for bi-directional communication between the patients and the medical emergency center (401). Such a device will transmit abnormalities alerts from the Holter/ECG to the medical dispatcher. The Holter/ECG device will then work in cellular network. The system will work in different wireless protocol systems including Integrated Digital Enhanced Network (IDEN), GSM, CDMA, etc.

IDEN is a preferable wireless system in the implementation of this invention since it is the best system for open way two-ways communication.

Using the wireless phone network will also allow to receive an exact location of the patient's whereabouts in case that there is a need to call an ambulance to that particular location. Most modern wireless phone networks can determine the location of the cellular handset with the accuracy of about 100 meters.

Patient's exact location could also be detected through the use of the GPS technology. For that, a special GPS receiver/transmitter will be further integrated within the device (402).

In case that an abnormality has been detected and an abnormality alert will be created, the medical emergency center (403) will send, in case of need, an emergency medical support, such as an ambulance to the patient (404). The medical ambulance will be called to the patient's most recent location obtained by the means of wireless network location and/or GPS-based location. The system will check the patient's current location and location of each ambulance and the nearest ambulance will be sent.

Figure 5:
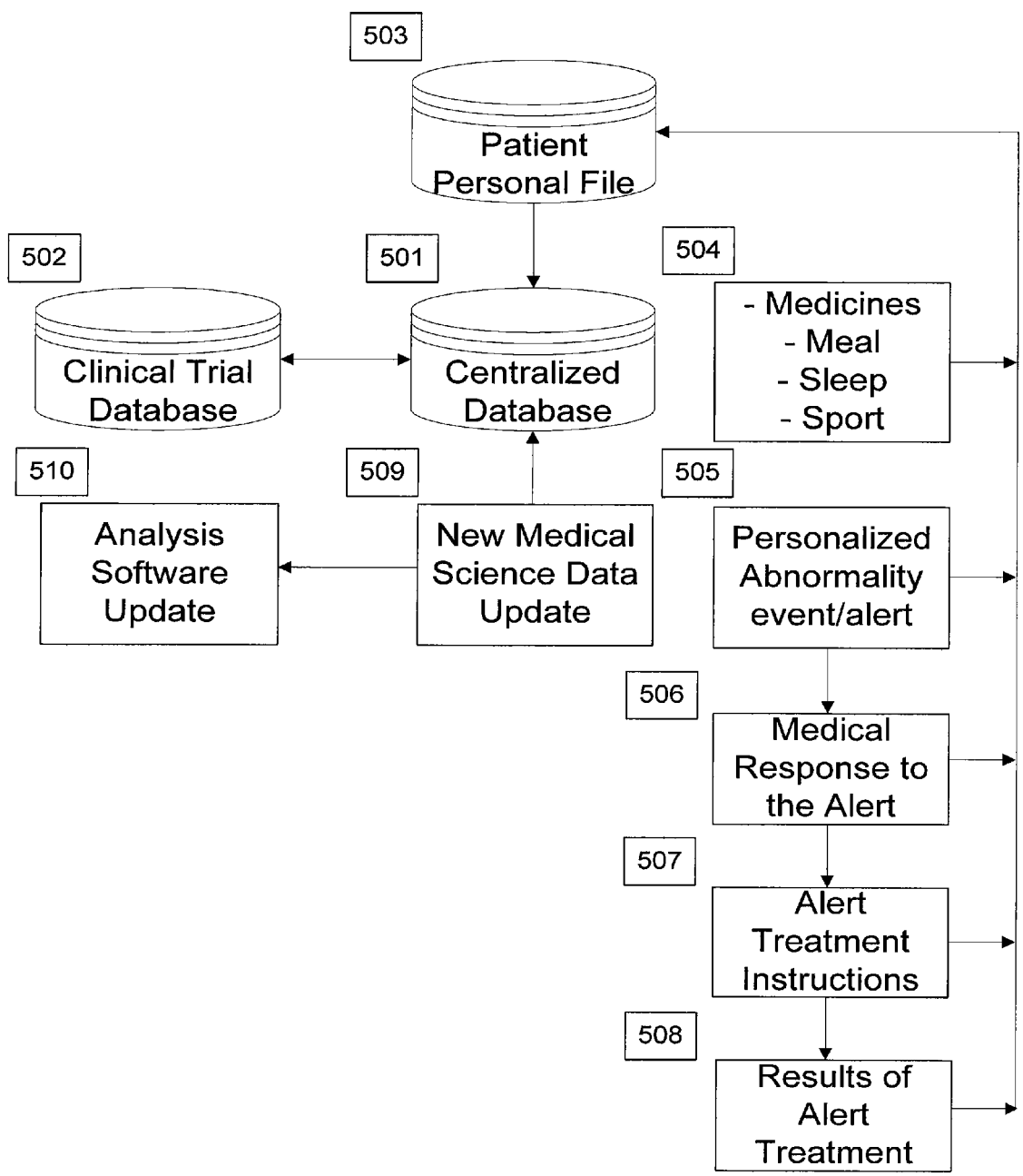
FIG. 5 provides a graphical illustration of the database and data movement in the invented system.

The system will further include a centralized medical database (501) where personal medical records for each patient will be stored, and to where all cardiological alerts and other cardiological data will arrive. Thus, FIG. 5 provides for databases and data movement in the system.

Such centralized database will be available for viewing, monitoring and analysis both on-location and through the Internet. For the Internet use, a special web-based portal will be developed.

An extensive statistical work will be applies to analyze such data for each patient separately and for all patients together as certain statistical averages and other statistics will be created. The latter will be helpful in producing clinical trials and for feeding clinical trial companies and pharmaceutical companies, in particular, with the medical data of each patient. For that a special clinical trial database interconnected with the centralized database will be created (502).

Full information database of all patients will be also produced as well as statistical parameters in regard to certain levels of cardiological activity and, particular cardiological parameters to suit a certain clinical trial need. For example, some pharmaceutical firm may require an adverse events database records for patients taking some sort of medicines that they develop or already developed.

For each patient enrolled, a medical file on record in a medical dispatcher center will be created (503). This medical file of the patient will include a full medical history of the patient, including a history of cardiovascular abnormalities, history of surgery operations and procedures, normal levels of psychological and cardiovascular parameters, such as pulse, blood pressure, etc. In particular, the patient medical record will include personal thresholds to determine if the event is irregular for the particular patient.

Information on medicine taken, on meals taken, on sleep and sports activities will be provided to the patient's personal file (504) and to the centralized database through wireless communication.

Abnormalities alerts data (505) as well as medical response to the alert data (506), alert treatment data (507) and results of alert treatment (medical condition after the treatment) (508) will also be provided to the patient's personal file and to the centralized database through wireless communication.

Besides regular updates on patients and abnormalities events, new medical scientific data update will be inputted to the centralized database (509) to keep it updated with the latest medical science developments (discoveries of new diseases, new methods of treatment, etc.). The new medical scientific data update will be also provided to the analysis software and will be consequently updated at patient's Holter/ECG device (510).

Figure 6:
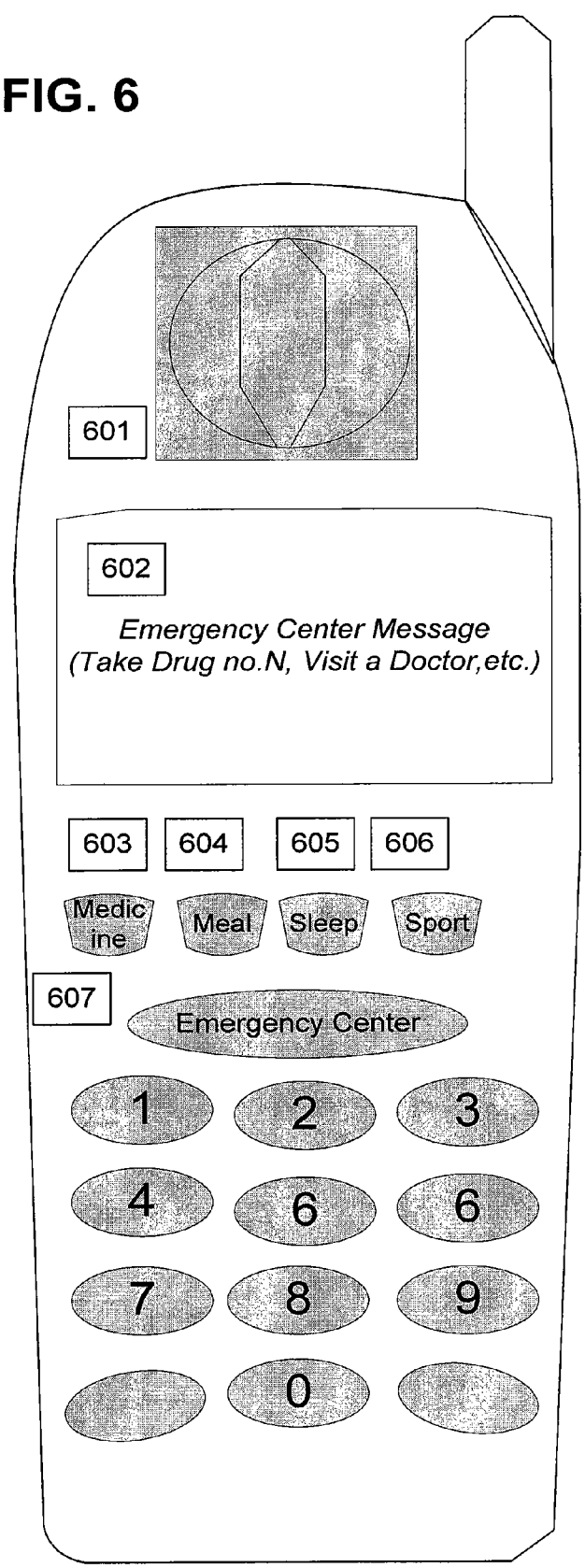
FIG. 6 provides a graphical illustration of the wireless device's display panel.
Figure 7:
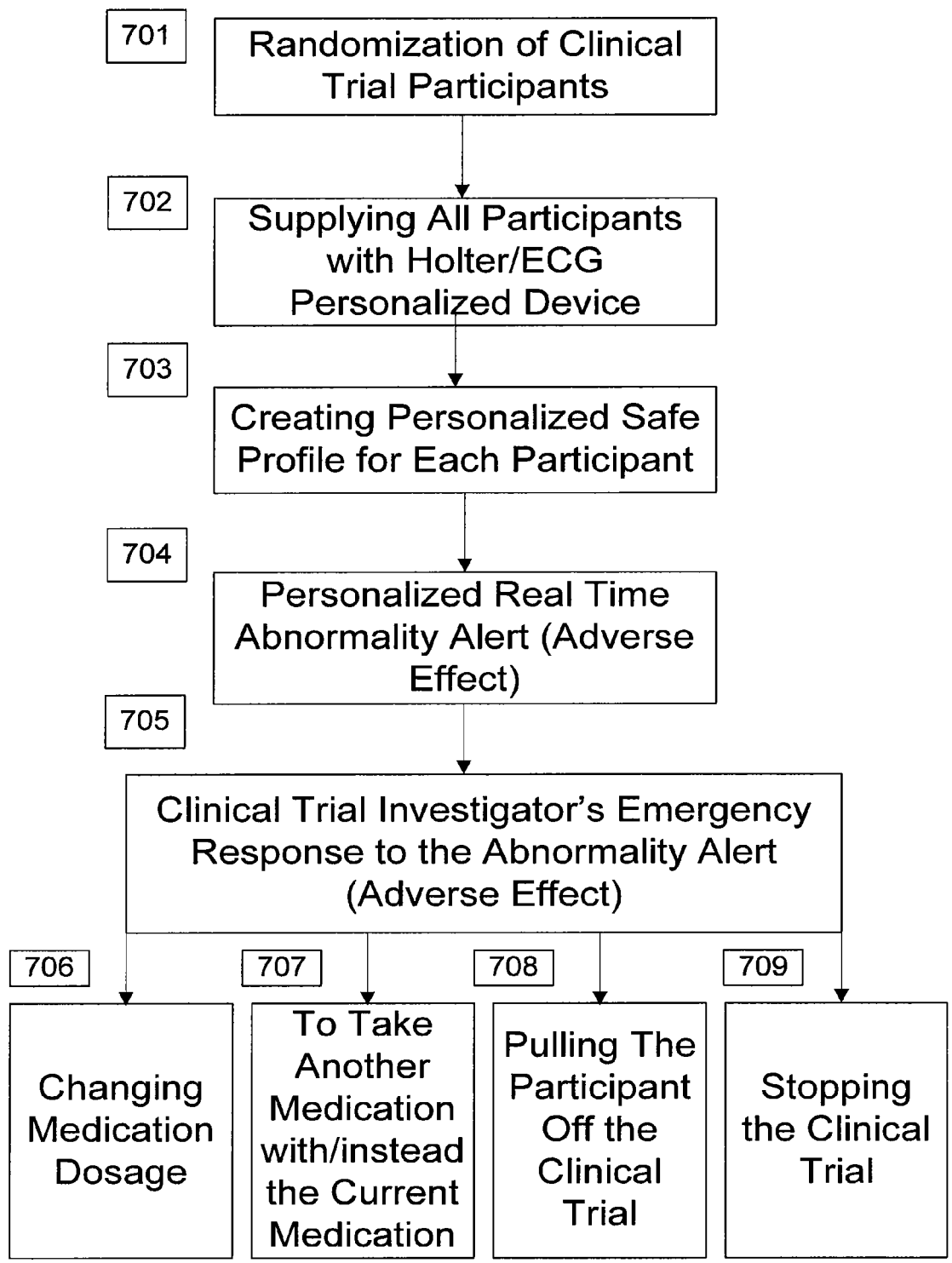
FIG. 7 provides a graphical illustration of the clinical trial management system.

FIG. 6 provides a graphical illustration of the wireless device and especially of it display panel. In the preferred embodiment the display unit could be a color LCD or a touch screen color display device easily accessible to the patient (601).

The cardiological abnormalities alert signals could also be shown on the screen of such patient's wireless device (602). This would be done according to patient's express will to receive the alerts or not. Some patient's may choose to not accept to receive such alerts on their device from psychological reasons.

To help obtaining more accurate cardiological information, the wireless device of the patient will also be equipped with four custom-produced buttons:

Medicines (603)
Meal (604)
Sleep (605)
Sport (606)

Clicking on the Medicines button will open several submenus where in each submenu there will be a name of each medicine that the patient takes. For that, the patient will submit information on the medicines he intakes when he initially enrolls into the system. After the patient takes that particular medicine, he will press on the medicine taken button for that particular medicine. Immediately, this information will be transferred using the wireless phone system to the central patients database and will be stored there in the file of that particular patient.

In addition "real-time adaptive approach" of the invention allows for instant modification of parameters of the clinical trial as it involves and as new clinical trial data is arrived. For example, the invention allows the study investigator to modify amount of medicine the certain participant takes, to order the participant to stop taking the medicine, to pull the participant of the trial, to pause or to stop a trial.

The invention further provides the capability of electronically managing submitted data to ensure that discrepancies are identified, as well as an interactive component for communicating with clinical sites to resolve data discrepancies, and a flexible, computer network-based (e.g., internet or intranet) system of reporting on data and performance indicators to sites, organizations managing the trial, and individuals involved with oversight.

It will be understood by those skilled in the art that these are merely exemplary components, and that the present invention is by no means limited to any particular implementation or combination of such systems.

Additionally, the patient may hit the Meal button after he starts/finishes his meal and may use the Sleep button when going to sleep and when waking up. This data will also be transferred using the wireless phone system to the central patients database and will be stored there in the file of that particular patient.

The patient may click on the Sport button whenever he starts or finishes his sporting or exercise activities. Such data will also simultaneously arrive to the central database and to the personal medical file situated there. That will help determine patient's diagnosis more accurately, and will also provide information for clinical trial use.

Such Medicines, Meal, Sleep, Sport data will assist in making the correct diagnosis and will also provide valuable information for the database in regard to clinical trial management companies, and especially for the pharmaceutical companies.

A special Emergency Center button (607) will be additionally installed at such a wireless device to enable the patient to call a medical emergency center with a press of one button without any delays.

The wireless device will have a multilingual capability to give an easy convenient access to most patients. A special rechargeable long-life battery should be used to provide a long lasting use of the wireless device.

So, more particularly, the present invention also relates to network architecture, and an associated communications protocol, for facilitating the efficient and reliable exchange of information between portable wireless devices and centralized monitoring stations.

The second major aspect of the invention describes a real-time automated system and apparatus for conducting clinical trials in the medical field by providing a fully integrated ability to handle real-time data collection from remotely situated participants of the clinical trial and by providing a real-time analysis and response to the data collected from the participants (graphically illustrated in FIG. 6). The invention particularly relates to a clinical trial of pharmaceutical substance (medicine, drug) providing clinical trial team with the ability to quickly react to the clinical trial data. This is especially useful for Phases I, II, III of the clinical trial. The invention looks to be particularly useful for Phase III of the clinical trial since Phase III studies generally involve randomized controlled large patient groups (300-3,000 or more depending upon the disease/medical condition studied). Phase III studies normally conducted on the "multicenter" basis, meaning that patients are situated at different locations, and sometimes even in different countries. Because of their size and comparatively long duration, Phase III trials are the most expensive, time-consuming and difficult trials to design and run, especially in therapies for chronic medical conditions. The invented system and apparatus could also be used for Phase IV trial (also known as Post Marketing Surveillance Trial) that involves the safety surveillance (pharmacovigilance) and ongoing technical support of a drug after it receives permission to be sold.

Since the invented system is designed to respond to changing circumstances is a central part of being able to successfully handle a clinical trial, the invention provides a "real-time adaptive approach" to conducting clinical trials. An adaptive approach to clinical trial means a system for providing automatic real-time medical response in clinical trials in medical field to detection of risks of adverse effects resulting from use of at least one medication, based on automatic cardiac abnormality alert detection from the Holter/ECG data.

In most clinical trials there are more than one medication or medical procedure being tested, in others just there is just one medication or medical procedure being trialed. So, in every clinical trial it is necessary to collect previously taken medical input data regarding that/those medication or medical procedure.

Then, for each medication/s or medical procedure a safe profile is determined, and safe profile parameters are defined then. Such safe profile parameters will be determined individually for every trial participant enrolled into the clinical trial based on his initial enrollment data.

A total number of enrolled trial participants will be determined before the start of the clinical trial. Then, the participants will be randomized and two or more randomized groups of participants will be created. Following the randomization, the system will determine which trial participants receive the pharmaceutical substance/procedure as part of the clinical trial and which trial participants receive a placebo (701).

Then the participants from both groups will receive permanent wireless Holter/ECG devices (702). The participants will also receive a login/password credentials to be able to access the clinical trial website and to have the ability to receive orders from clinical trial investigators through the Internet. Such devices are described above in more details.

The abovementioned device will detect personalized abnormalities in cardiac parameters of clinical trial participants based on individual profile parameters of each participant. Additionally, special personalized safe profile parameters in regard to clinical trial treatment will be concluded for each participant. Such individual safe profile parameters will take into consideration general safe parameters for the treatment in conjunction with personal health parameters of the participant (703).

For the abnormality alert detected that is outside of the personal safe profile parameters for the particular participant, the abnormality alert will be assessed in combination with other drugs, foods, vitamins, sporting activities and other parameters data and it will be determined if an alert constitutes adverse effect risk requiring emergency medical response (704).

Based on personalized abnormality alert detection, clinical trial investigators team will choose from a variety of possible medical responses based on the severity and frequency of adverse effect cases (705). For one, clinical trial investigators may decide to order the participant to change the dosage of the medication/medical treatment (706). Another option is to transmit the clinical trial participant an order to stop taking the said medication/medical treatment and/or start taking another medication/medical treatment instead (707). If there are serious adverse effect risks that may risk clinical trial participant's health or even life, the investigators may transfer the order to pull the participant out of the clinical trial (708). All those orders may be transmitted wirelessly using the two-way communication capabilities of the wireless device. For another option, those orders may be transmitted by phone or through the Internet.

If clinical trial investigators team decide that the number/severity of adverse effects risks is critical, they may decide to stop the clinical trial and, consequently, send an appropriate wireless/phone/web order to all clinical trial participants (709).

The invented system further includes the feature of providing a number of online/offline reports, including medical, financial and others, relating to the clinical trial conducted.

What is claimed:

1. A method for providing cardiovascular personalized patient alerts for a plurality of patients, comprising the steps of:
   a) maintaining physiological data and cardiac data for each of said plurality of patients, respectively, said cardiac data selected from the list consisting of ECG, EKG, blood pressure, heart rate;
   b) creating personalized resting alert thresholds for each of the patients, respectively, based on the physiological data and the cardiac data when each of said patients are respectively at rest;
   c) providing each patient with a respective wireless Holter/ECG-type device which is worn on each patient, each Holter/ECG-type device having respective buttons including a Medicine button for pressing when the patient has taken any particular medicine, a Sports button for pressing when the patient will be engaged in a sporting activity; a Meal button for pressing when the patient will have a meal and; a Sleep button for pressing when the patient will start/finish his sleep;

d) providing each of said patients with respective abnormality alert thresholds, wherein each of said thresholds is respectively different between each of said patients based on each patients' respective physiological data or cardiac data wherein the alert thresholds being exceeded is detected based on said physiological data or cardiac data which is obtained;

e) updating said alert thresholds provided in step d) for each of said patients, based on said respective resting alert thresholds, respective cardiac data provided by each Holter/ECG-type device as a result of monitoring each of said patients, respective abnormality alert thresholds and actuation of said respective buttons;

f) generating, without human involvement, a respective diagnosis for each of said patients based on data provided by each of said Holters/ECGs, said updated alert thresholds, and whether any of said buttons have been pushed, wherein said respective diagnosis is generated by a respective one of said Holters/ECGs prior to step g); and;

g) transmitting said respective diagnosis from said wireless Holter/ECG-type device, for a medical response to be provided at a location where one of said patients is located if said generated diagnosis is predetermined to be responded to by the medical response, wherein said medical response includes requesting providing of an ambulance to said location where said one of said patients is located.

2. The method of claim 1, further comprising the step of:
h) storing said physiological data and said cardiac data for each of said patients, respectively, at a centralized database.

3. The method of claim 2, wherein step h) further comprises:
signaling via a cellular network to the centralized database at a medical emergency center.

4. The method of claim 2, wherein the wireless device further includes means for analyzing statistical data received from the centralized database.

5. The method of claim 4, wherein the wireless device includes means for sending the analyzed statistical data to clinical trial providers in a format acceptable to the clinical trial providers.

6. The method of claim 1, wherein each respective wireless Holter/ECG-type device includes a cellular mobile telephone, a multimedia phone or a personal digital assistant (PDA).

7. The method of claim 1, further comprising the step of:
i) determining an exact location of each wireless Holter/ECG-type device by obtaining a wireless phone location of the wireless device or a GPS equipment-based location of the wireless device.

8. The method of claim 1, wherein step g) further comprises sending an ambulance in response to the transmitting.

9. The method of claim 8, wherein an exact location of each wireless device is obtained by obtaining a wireless phone location of each wireless device or a GPS equipment-based location of each wireless device, and the ambulance is sent to each patients' exact location.

10. The method of claim 1, wherein the wireless device further includes a blood pressure apparatus, and further comprising the step of:
transferring said cardiac data including blood pressure after the signaling of step f).

11. The method of claim 1, further comprising blood pressure measuring means, such means comprising:
an inflatable cuff chamber operable to be inflated during an inflation interval and deflated during a deflation interval;
a sensor coupled to said inflatable cuff chamber and configured to measure a blood pressure; and
a control electronic module configured for controlling the operation of said inflatable cuff chamber and said sensor.

12. The method of claim 11, further comprising the step of:
taking a permanent continuous blood pressure measurement in predetermined time-intervals.

13. The method of claim 12, further comprising the step of:
transmitting wirelessly a personalized abnormality blood pressure alert to the medical emergency center based on personalized blood pressure measurements thresholds, the said thresholds being determined individually for each patient, wherein threshold limits are limit of normal blood pressure for the patient.

14. The method of claim 13, further comprising the steps of:
obtaining as an input from the centralized database initial patient personalized blood pressure emergency alerts thresholds;
obtaining as an input real-time cardiological data of the patient from the continuous blood pressure measurement, including the initial patient personalized blood pressure emergency alerts thresholds;
updating said initial patient personalized blood pressure emergency alerts thresholds with the real-time cardiological data.

15. The method of claim 1, wherein step d) includes the step of creating the updated alert thresholds based on said cardiac data which is provided after said respective buttons have been actuated.

16. A method according to claim 1, wherein said medical response includes sending a closest ambulance to said patients' location based on said GPS equipment-based location.

17. A method for monitoring cardiovascular activity of patients, comprising the steps of:
creating personalized resting alert thresholds for each of said patients, respectively, based on physiological data and cardiac data when each of said patients are respectively at rest;
obtaining data relating to the cardiovascular activity of the patients;
generating abnormality alert thresholds for said patients based on said data and said resting alert thresholds, and
providing each of said patients with respective abnormality alert thresholds, wherein each of said thresholds is respectively different between each of said patients based on each patients' respective physiological data or cardiac data wherein the alert thresholds being exceeded is detected based on said physiological data or cardiac data which is obtained;
detecting, without human involvement, abnormalities in the cardiovascular activity of the patient by comparing the obtained data with personalized cardiovascular activity thresholds for the patient;
generating alerts based on the detected abnormalities;
modifying the thresholds based on the thresholds being previously exceeded;
generating a diagnosis prior to transmitting the alerts to the medical emergency center;
transmitting the alerts to a medical emergency center over a wireless network; and receiving a response from the medical emergency center over the wireless network.

18. A method according to claim 17, wherein a closest ambulance is sent to said patient based on GPS data transmitted when said alerts are transmitted.

19. A method for providing real-time medical response to abnormal cardiovascular activity of patients, comprising the steps of:
- creating personalized resting alert thresholds for each of the patients, respectively, based on physiological data and cardiac data when each of said patients are respectively at rest;
- providing to the patients recorder devices for continuously monitoring the cardiovascular activity of the patient, said recorder device for generating abnormality alert thresholds;
- providing each of said patients with respective abnormality alert thresholds, wherein each of said thresholds is respectively different between each of said patients based on each patients' resting alert thresholds and each patients' respective physiological data or cardiac data wherein the alert thresholds being exceeded is detected based on said physiological data or cardiac data which is obtained;
- receiving, without human involvement, at a medical emergency center a) alerts indicating the abnormal cardiovascular activity of the patients from the recorder devices via a wireless network, and b) diagnosis; and
- issuing the medical response to the patient in real-time based on the received alerts.

20. A method according to claim 19, wherein a closest ambulance is sent to said patient based on GPS data transmitted when said alerts are transmitted.

* * * * *